(12) United States Patent
Gaitonde et al.

(10) Patent No.: US 8,664,390 B2
(45) Date of Patent: Mar. 4, 2014

(54) PROCESS FOR THE INTRODUCTION OF HYDROXYETHOXY SIDE CHAIN IN BOSENTAN

(75) Inventors: Abhay Gaitonde, Maharashtra (IN); Bindu Manojkumar, Maharashtra (IN); Sandeep Sonawane, Maharashtra (IN); Dattatrey Kokane, Maharashtra (IN); Sandeep Mekde, Maharashtra (IN); Dattatraya Shinde, Maharashtra (IN); Prakash Bansode, Maharashtra (IN)

(73) Assignee: Generics (UK) Limited, Hertfordshire (GB)

( * ) Notice: Subject to any disclaimer, the term of this patent is extended or adjusted under 35 U.S.C. 154(b) by 442 days.

(21) Appl. No.: 12/665,997

(22) PCT Filed: Jun. 27, 2008

(86) PCT No.: PCT/GB2008/050517
§ 371 (c)(1),
(2), (4) Date: Jun. 1, 2010

(87) PCT Pub. No.: WO2009/004374
PCT Pub. Date: Jan. 8, 2009

(65) Prior Publication Data
US 2010/0249162 A1    Sep. 30, 2010

(30) Foreign Application Priority Data
Jun. 29, 2007 (IN) .......................... 1245/MUM/2007

(51) Int. Cl.
*C07D 403/04* (2006.01)
*A61K 31/505* (2006.01)

(52) U.S. Cl.
USPC ........................................................ 544/296

(58) Field of Classification Search
USPC .......................................... 514/269; 544/296
See application file for complete search history.

(56) References Cited

U.S. PATENT DOCUMENTS

| | | | |
|---|---|---|---|
| 5,292,740 A | 3/1994 | Burri et al. | |
| 5,739,333 A | 4/1998 | Yamada et al. | |
| 6,136,971 A | 10/2000 | Harrington et al. | |
| 8,288,401 B2 | 10/2012 | Gaitonde et al. | |
| 2008/0188663 A1 | 8/2008 | Kumar et al. | |
| 2008/0242687 A1 | 10/2008 | Gant et al. | |
| 2009/0156811 A1 | 6/2009 | Taddei et al. | |
| 2009/0291974 A1 | 11/2009 | Zhu | |
| 2010/0261742 A1 | 10/2010 | Gaitonde et al. | |
| 2010/0331352 A1 | 12/2010 | Gaitonde et al. | |
| 2011/0014291 A1 | 1/2011 | Dixit et al. | |

FOREIGN PATENT DOCUMENTS

| | | |
|---|---|---|
| CA | 2 071 193 | 5/1992 |
| CN | 1425007 | 6/2003 |
| CN | 101062897 | 10/2007 |
| CN | 101175484 A | 5/2008 |
| EP | 0 526 708 | 2/1993 |
| EP | 0 526 708 B1 | 2/1993 |
| EP | 0 743 307 A | 9/2001 |
| EP | 0 743 307 B1 | 9/2001 |
| EP | 2 072 503 | 6/2009 |
| IN | 1245/MUM/2007 | 6/2007 |
| WO | WO 01/36384 | 5/2001 |
| WO | WO 01/43742 | 6/2001 |
| WO | WO 01/55120 | 8/2001 |
| WO | WO 2004/076443 | 9/2004 |
| WO | WO 2004/081016 | 9/2004 |
| WO | WO 2004/087660 | 10/2004 |
| WO | WO 2006123285 A2 | 11/2006 |
| WO | WO 2008/135795 | 11/2008 |
| WO | WO 2009/047637 | 4/2009 |
| WO | WO 2009/053748 | 4/2009 |
| WO | WO 2009/093127 | 7/2009 |
| WO | WO 2009/095033 | 8/2009 |
| WO | WO 2009/098517 | 8/2009 |
| WO | WO 2009/112954 | 9/2009 |
| WO | WO 2010/061210 | 6/2010 |

OTHER PUBLICATIONS

Harrington, Peter J. et al., "Research and Development of a Second Generation Process for Bosentan", Organic Process Research & Development, vol. 6, 2002, pp. 120-124, XP002495602.
D.J. Brown et al., "Heterocyclic Compounds—The Pyrimidines", 1994, John Wiley & Sons, New York, 20723, XP 002495603, pp. 3967-401.
Boulton, A.J. et al., "Comprehensive Heterocyclic Chemistry", vol. 3, 1984, Pergamon Press, Oxford, 125880, XP002495604, p. 98, pp. 101 and 134.
International Search Report PCT/GB2008/05057 dated Sep. 26, 2008 (6 pgs.).
Background information for the Oct. 2002 ACPS Meeting. Scientific Considerations of Polymorphism in Pharmaceutical Solids: Abbreviated New Drug Applications.
C. Boss et al., Bioorganic Medicinal Chemistry Letters, 13, 951-954 (2003)
Dunitz et al., Acc. Chem. Res., vol. 28, 1995, pp. 193-200

(Continued)

*Primary Examiner* — James O Wilson
*Assistant Examiner* — Ebenezer O Sackey
(74) *Attorney, Agent, or Firm* — Scott D. Rothenberger; Fulbright & Jaworski L.L.P.

(57) ABSTRACT

The present invention relates to an improved process for the preparation of bosentan. In particular it relates to a process for preparing bosentan substantially free from the dimer impurity of formula (II) and the 6-hydroxy impurity of formula (III). The invention also relates to a pharmaceutical composition comprising bosentan and its use in the treatment of endothelin-receptor mediated disorders.

4 Claims, No Drawings

(56) References Cited

OTHER PUBLICATIONS

J.H. Pupart, Encyclopaedia of pharmaceutical technology, 1362-1369.
Journal of the American Society for Mass Spectrometry, 1999, vol. 10(12), pp. 1305-1314.
"Protection of a reactive group" IUPAC Gold Book 2011.
S.R. Vippagunta et al., Advancved Drug Delivery Reviews, vol. 48, 2001, pp. 3-26.
Swanepoel et al., European Journal of Pharmaceuticals and Biopharmaceutics, 2003, vol. 55, pp. 345-349
Uses of X-ray Powder Diffraction in the Pharmaceutical industry; in Pharmaceutical Sciences Encyclopedia: Drug Discovery, Development, and Manufacturing, Edited by Shayne C. Gad, John Wiley & Sons, 2010.
Newport Premium Report, Bosentan monohydrate, downloaded Sep. 4, 2013, 2 pages.
Background Information for the Oct. 2002 ACPS Meeting. Scientific Considerations of Polymorphism in Pharmaceutical Solids: Abbreviated New Drug Applications.
Bioorganic & Medicinal Chemistry, vol. 9, 2001, pp. 2955-2968.
Bosentan Wikipedia extract 26.6.08.
C. Boss et al., Bioorganic Medicinal Chemistry Letters, 13, 951-954 (2003).
Chemblink webpage re 4,6-dichloro-5-(2-methoxyphenoxy)-2,2'-bipyrimidine 19.1.09.
Chemburkar et al., Organic Process Research & Development, vol. 4, 2000, pp. 413-417.
Chen et al., Chemical Reagent, vol. 21(6), pp. 339-346.
Chinese Journal of Medicinal Chemistry, vol. 15, 2005, pp. 230-233.
Chromatographia, 2002, vol. 55, pp. S115-S119.
Dunitz et al., Acc. Chem. Res., vol. 28, 1995, pp. 193-200.
EMEA 2005.
J.H. Pupart, Encyclopaedia of pharmaceutial technology, 1362-1369.
J.K. Guillory, Generation of Poly morphs, Hydrates, Solvates and Amorphous Solids, in Polymorphism in Pharmaceutical Solids, pp. 183-226 (H.G. Brittain ed. 1999).
J. Lang, Application Note, Thermal Analysis, Perkin Elmer, 2010.
Journal of Chromatography A, 1995, vol. 712(1), pp. 75-83.
Journal of the American Society or Mass Spectrometry, 1999, vol. 10(12), pp. 1305-1314.
Journal of Mass Spectrometry, 1996, vol. 31, pp. 69-76.
Journal of Chromatography B, 2000, vol. 749(1), pp. 67-83.
Martinez-Oharriz et al., Journal of Pharmaceutical Sciences, 1994, vol. 83(2), pp. 174-177.
Modern Drug Discovery, Mar. 2000, p. 53, K. Knapman.
Neidhard W et al., Chimia, vol. 50, 1996, pp. 519-524.
Organic Syntheses, coll. vol. 5, p. 932 (1973); vol. 49, p. 93 (1969).
"Protection of reactive group" IUPAC Gold Book 2011.
S.L. Morisette et al., Advanced Drug Delivery Reviews, vol. 56, 2004, pp. 275-3000.
S.R. Vippagunta et al., Advanced Drug Delivery Reviews, vol. 48, 2001, pp. 3-26.
Swanepoel et al., European Journal of Pharmaceuticals and Biopharmaceutics, 2003, vol. 55, pp. 345-349.
Topics in Current Chemistry, vol. 198, 1998, pp. 163-208.
T.W. Greeene & P.G.M. Wuts, Protective Groups in Organic Synthesis ($3^{rd}$ Ed., John Wily & Sons, 1999) re hydroxyl protection.
UC Santa Barbara, Materials Research Laboratory; MDSC Manual; http://www.mrl.ucsb.edu/sites/default/files/mrl_docs/instruments/MDSCManual.pdf.
Uses of X-ray Power Diffraction in the Pharmaceutical Industry; in Pharmaceutical Sciences Encyclopedia: Drug Discovery, Development, and Manufacturing, Edited by Shane C. Gad, John Wiley & Sons, 2010.
X-ray diffraction; in US Pharmacopeia 29, Chapter 941.
Wu et al., Journal of Pharmaceutical Sciences, 1994, vol. 83(10), pp. 1404-1406.
Bernstein, "Polymorphism in Molecular Crystals", Table 4.6, 2002, 3 pages.
Metabolite Services at JIC, Mar. 8, 2009, www.jic.ac.uk/services/metabolomics/topics/lcms/why.htm.

PROCESS FOR THE INTRODUCTION OF HYDROXYETHOXY SIDE CHAIN IN BOSENTAN

CROSS-REFERENCE TO RELATED APPLICATION(S)

This application is a Section 371 National Stage Application of International No. PCT/GB2008/050517, filed 27 Jun. 2008 and published as WO 2009/004374 A2 on 8 Jan. 2009, which claims priority from the India Application 1245/MUM/2007, filed 29 Jun. 2007, the contents of which are incorporated herein in their entirety for all purposes.

FIELD OF THE INVENTION

The present invention relates to an improved process for the preparation of bosentan. In particular it relates to a process for preparing bosentan substantially free from the dimer impurity of formula (II) and the 6-hydroxy impurity of formula (III). The invention also relates to a pharmaceutical composition comprising bosentan and its use in the treatment of endothelin-receptor mediated disorders.

BACKGROUND OF THE INVENTION

Bosentan, represented by structural formula (I) and chemically named 4-tert-butyl-N-[6-(2-hydroxyethoxy)-5-(2-methoxyphenoxy)-2-(2-pyrimidinyl)-pyrimidin-4-yl]-benzene-sulfonamide is an endothelin receptor antagonist. It is used for the treatment of endothelin-receptor mediated disorders, in particular circulatory and cardiovascular disorders such as hypertension, ischemia, pulmonary hypertension, vasospasm and angina pectoris. The marketed product comprising bosentan, Tracleer®, is indicated for the treatment of pulmonary arterial hypertension (PAH) to improve exercise capacity and symptoms in patients with grade III functional status.

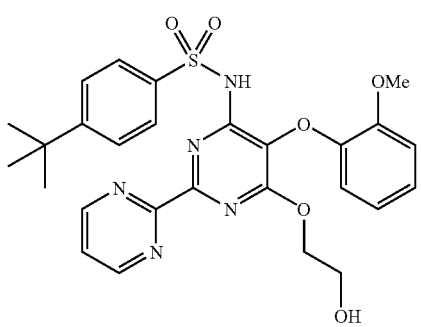

(I)

Bosentan (I) was first described in U.S. Pat. No. 5,292,740. The preparation method involves two steps (shown in Scheme 1) starting from the dichloro compound (1). The second reaction step is carried out in ethylene glycol with sodium metal used as the base at a temperature of 100-110° C. The process results in bosentan (I) of about 69-73% purity. The purity is further increased by column chromatography, however, this reduces the yield such that the overall yield of bosentan (I) from the dichloro compound (1) is only about 30-40%. Further, use of sodium metal has disadvantages. Apart from being inconvenient to handle due to moisture sensitivity, sodium metal is also a safety hazard during handling, storage and quenching.

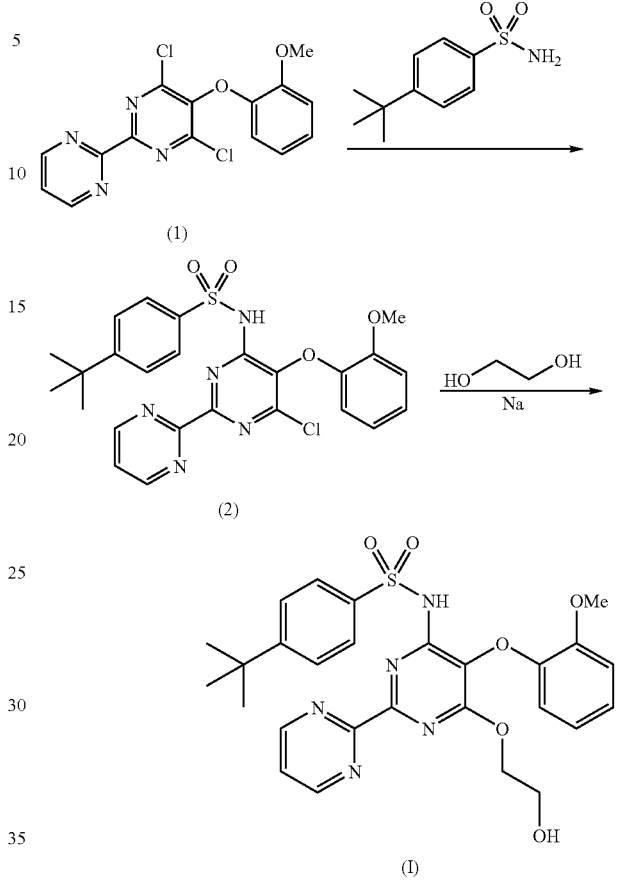

Scheme 1

One of the problems to be overcome in the preparation of bosentan (I) is the formation of the undesired ethylene glycol bis-sulfonamide dimer of formula (II) in which two molecules of the pyrimidine monohalide (2) are coupled with one molecule of ethylene glycol. The removal of this impurity requires costly and laborious separation steps. To minimize the formation of this impurity a large excess of ethylene glycol can be used. However, using a large excess of ethylene glycol is impractical on a large industrial scale, because ethylene glycol is toxic and its high boiling point means that its removal by distillation is energy and time consuming.

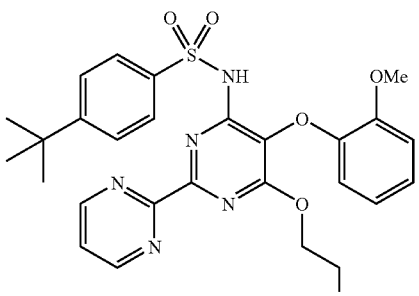

(II)

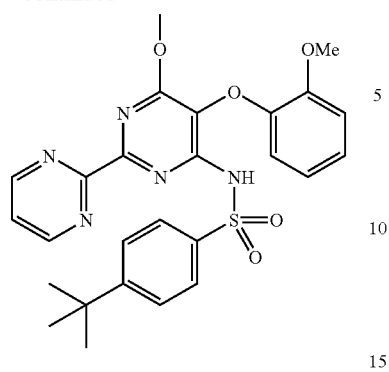

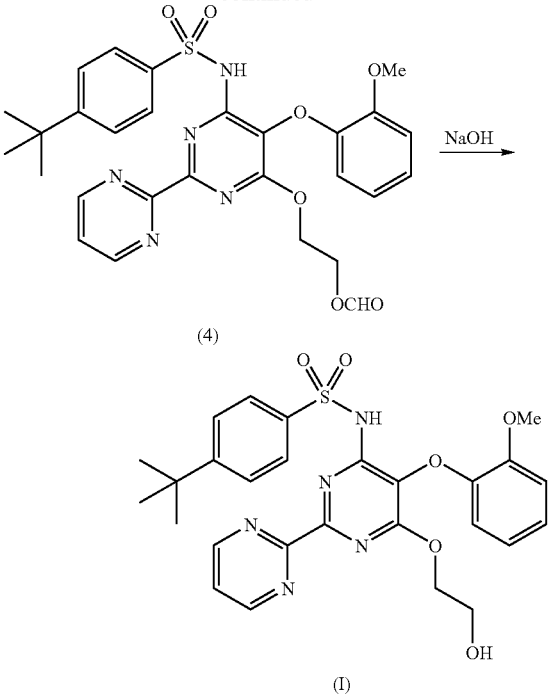

(4)

(I)

U.S. Pat. No. 6,136,971 discloses a process (shown in Scheme 2) for the preparation of bosentan with high purity (>99%) and solves the problem of the dimer formation by utilising a mono-protected 1,2-diheteroethylene anion. In a particularly preferred aspect, the protecting group is a tert-butyl group used to protect one hydroxyl group of ethylene glycol as an ether. The protecting group is then removed using formic acid to produce a formyloxy-protected ethylene glycol sulfonamide derivative (4). Treatment of this compound (4) with a base, preferably sodium hydroxide, then produces an ethylene glycol sulfonamide derivative, bosentan (I), containing a free hydroxy group. The skilled person will appreciate that such a process is laborious, as it involves a number of steps relating to the protection and deprotection of ethylene glycol as the tert-butyl ether. Consequently, the process is not suitable for commercial manufacture.

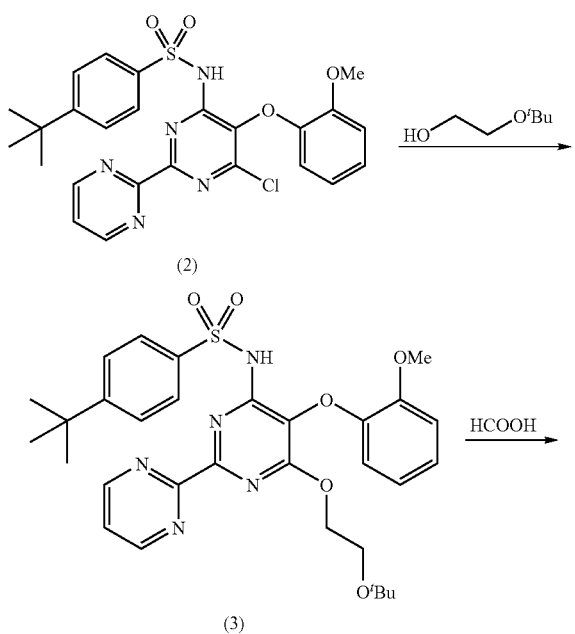

In view of the above disadvantages associated with the prior art, there is a need for an improved process for the preparation of bosentan which does not involve multiple steps and further eliminates the need for cumbersome purification techniques, is economical and high yielding, and which provides bosentan with a high degree of purity.

It has further been noted that the prior art processes need to employ high temperatures in the preparation of bosentan. This further adds to the inefficiency and high processing costs. The high temperatures also increase the likelihood of impurities being formed during manufacture. Thus there is also a need for a process wherein the temperatures employed during the manufacturing process are such as to avoid the prior art problems.

SUMMARY OF THE INVENTION

Accordingly, in a first aspect according to the invention there is provided a process for the preparation of bosentan (I), comprising the steps of:
(a) providing a mixture of ethylene glycol and hydroxide ions;
(b) adding 4-tert-butyl-N-[6-chloro-5-(2-methoxyphenoxy)-2-(2-pyrimidinyl)-pyrimidin-4-yl]-benzenesulfonamide (2) to the mixture from step (a); and
(c) isolating bosentan (I) from the mixture obtained in step (b).

In one embodiment the ethylene glycol is dissolved in an organic solvent, which preferably is selected from the group comprising: dimethyl sulfoxide, tetrahydrofuran, acetonitrile, dimethylformamide and dimethylacetamide. Most preferably, the organic solvent is tetrahydrofuran.

In another embodiment the ethylene glycol is dissolved by heating the organic solvent. Further embodiments provide a process according to the first aspect, wherein the mixture from step (b) is heated to dissolve the 4-tert-butyl-N-[6-chloro-5-(2-methoxyphenoxy)-2-(2-pyrimidinyl)-pyrimidin-4-yl]-benzenesulfonamide. Preferably, the mixtures from steps (a) and (b) are heated independently to a temperature in the range of between about 40 and 95° C., most preferred is a temperature in the range of between 65 and 75° C.

In a further embodiment the hydroxide ions are provided by the group comprising: alkali metal hydroxides, alkali earth metal hydroxides and ammonium hydroxides, preferably by alkali metal hydroxides. Further preferred embodiments provide a process, wherein the alkali metal hydroxide is selected from the group comprising: sodium hydroxide, potassium hydroxide and lithium hydroxide. In a most preferred embodiment the alkali metal hydroxide is sodium hydroxide.

Another embodiment according to the first aspect is provided, wherein the mixture from step (b) is cooled, preferably the mixture is cooled to a temperature of between 0 and 25° C., most preferably to about 10° C.

In yet another embodiment an organic or inorganic acid is added to the mixture from step (b). Preferably the inorganic acid is selected from the group comprising: hydrochloric, hydrobromic, hydroiodic, nitric, sulfuric, and phosphoric acid. In alternative embodiments the organic acid is selected from the group comprising: an aliphatic carboxylic acid, an aromatic carboxylic acid, and a sulfonic acid. Preferably the acid is selected from the group comprising: formic, acetic, propionic, succinic, camphorsulfonic, citric, fumaric, gluconic, lactic, malic, mucic, tartaric, para-toluenesulfonic, glycolic, glucuronic, maleic, furoic, glutamic, benzoic, anthranilic, salicylic, phenylacetic, mandelic, pamoic, methanesulfonic, ethanesulfonic, pantothenic, benzenesulfonic (besylate), stearic, sulfanilic, alginic, galacturonic, 2-ethanedioic (oxalic), 3-propanedioic (malonic), 4-butanedioic (succinic), 5-pentanedioic (glutaric), 6-hexanedioic (adipic), cis-butenedioic (maleic) and trans-butenedioic (fumaric), dihydroxybutanedioic (tartaric), 2-hydroxypropane-1,2,3-tricarboxylic (citric), pimelic, suberic, azelaic, and sebacic acid. Monocarboxylic acids that may be useful in the working of the present invention include, but are not limited to, methanoic (formic), ethanoic (acetic), propanoic (propionic), butanoic (butyric), pentanoic (valeric), hexanoic (caproic), heptanoic (enanthic), 2-hydroxypropanoic (lactic), and 3-benzyl-2-propenoic (cinnamic) acid. Most preferably the acid is tartaric acid. Preferably the acid is added as a solution, preferably in water, to the mixture from step (b).

In a second aspect according to the invention there is provided a process for the preparation of bosentan (I), comprising the steps of:
(a) heating a mixture of ethylene glycol and sodium hydroxide in tetrahydrofuran until the ethylene glycol has substantially dissolved;
(b) adding to the solution from step (a) 4-tert-butyl-N-[6-chloro-5-(2-methoxyphenoxy)-2-(2-pyrimidinyl)-pyrimidin-4-yl]-benzenesulfonamide (2) and heating the mixture;
(c) cooling the mixture from step (b) and adding a solution of tartaric acid; and
(d) isolating the resulting solid.

In one embodiment, the mixture in step (b) is heated to a temperature of between about 40 and 60° C., preferably the mixture is heated to about 50° C.

In another embodiment, the tetrahydrofuran is distilled out under vacuum.

In a further embodiment, the mixture in step (c) is cooled to a temperature of between about 0-20° C., preferably to about 10° C.

In yet another embodiment the resultant solid in step (d) is isolated by filtration.

Preferably the solid is further washed, most preferably with isopropyl alcohol, ethanol and water. In another embodiment, the solid is further dried, preferably under vacuum.

The process according to the first and second aspect of the present invention is preferably carried out on an industrial scale, preferably providing bosentan (I) in batches of about 50 g, 100 g, 500 g, 1 kg, 2 kg, 5 kg, 10 kg, 50 kg, 100 kg or more.

The process according to the first and second aspect of the present invention preferably provides bosentan (I) in a molar yield of 50%, 60%, 70%, 80%, 85% or more from 4-tert-butyl-N-[6-chloro-5-(2-methoxyphenoxy)-2-(2-pyrimidinyl)-pyrimidin-4-yl]-benzene-sulfonamide.

The process according to the first and second aspect of the present invention is preferably carried out at a temperature of 95° C., 90° C., 85° C., 80° C., 75° C., 70° C., 65° C., 60° C., 55° C. or less.

The process according to the first and second aspect of the present invention is preferably carried out using 200 eq, 150 eq, 110 eq or less of ethylene glycol relative to 4-tert-butyl-N-[6-chloro-5-(2-methoxyphenoxy)-2-(2-pyrimidinyl)-pyrimidin-4-yl]-benzenesulfonamide.

The process according to the first and second aspect of the present invention is preferably carried out without the use of sodium metal.

The process according to the first and second aspect of the present invention is preferably carried out without the use of chromatography.

The bosentan (I) obtained by the process according to the first and second aspect of the present invention is preferably substantially pure, preferably comprising less than about 5%, preferably less than about 3%, more preferably less than about 1% of any impurities (as measured by HPLC). Preferably the bosentan (I) comprises less than about 0.1%, preferably less than about 0.05% of the dimer impurity (II) (as measured by HPLC). Preferably the bosentan (I) comprises less than about 5%, preferably less than about 3%, more preferably less than about 1%, more preferably less than about 0.5%, and most preferably less than about 0.1% of the 6-hydroxy-sulfonamide impurity (III) (as measured by HPLC).

A third aspect of the invention provides bosentan comprising less than about 0.1%, preferably less than about 0.05% of the dimer impurity (II).

A fourth aspect of the invention provides bosentan comprising less than about 5%, preferably less than about 3%, more preferably less than about 1%, more preferably less than about 0.5%, and most preferably less than about 0.1% of the 6-hydroxy-sulfonamide impurity (III).

A fifth aspect according to the invention provides bosentan prepared according to a process of the present invention, comprising less than about 0.1%, preferably less than about 0.05% of the dimer impurity (II).

In a sixth aspect according to the invention there is provided bosentan prepared according to a process of the present invention, comprising less than about 5%, preferably less than about 3%, more preferably less than about 1%, more preferably less than about 0.5%, and most preferably less than about 0.1% of the 6-hydroxy-sulfonamide impurity (III).

A seventh aspect provides a use of bosentan according to any one of the preceding aspects and embodiments, in the manufacture of a composition for the treatment or prevention of an endothelin-receptor mediated disorder. In a preferred embodiment the disorder is pulmonary arterial hypertension.

An eighth aspect according to the invention provides a pharmaceutical composition comprising bosentan according to any one of the preceding aspects and embodiments, and at least one pharmaceutically acceptable excipient.

A ninth aspect provides a use of a pharmaceutical composition comprising bosentan according to the invention in the manufacture of a medicament for the treatment or prevention of an endothelin-receptor mediated disorder. In a preferred embodiment the disorder is pulmonary arterial hypertension.

A tenth aspect provides a method of treating or preventing an endothelin-receptor mediated disorder, comprising administering a therapeutically or prophylactically effective amount of bosentan according to the invention to a patient in need thereof. In a preferred embodiment the disorder is pulmonary arterial hypertension. Preferably the patient is a mammal, preferably a human.

DETAILED DESCRIPTION OF THE INVENTION

The present invention provides an efficient and economical synthesis of bosentan starting from 4-tert-butyl-N-[6-chloro-5-(2-methoxyphenoxy)-2-(2-pyrimidinyl)-pyrimidin-4-yl]-benzenesulfonamide, which is high yielding and affords the product with very high purity on a commercial scale.

The present inventors have explored the idea of using hydroxide ions as the base during the conversion of 4-tert-butyl-N-[6-chloro-5-(2-methoxyphenoxy)-2-(2-pyrimidinyl)-pyrimidin-4-yl]-benzenesulfonamide into bosentan (I). They surprisingly found that the use of hydroxide ions in a process according to the invention controlled the formation of the dimer impurity (II). Further, the use of hydroxide ions, which are most preferably provided by sodium hydroxide in this process, would be expected by the skilled person to result in the formation of the 6-hydroxy-sulfonamide represented by formula (III). The excess of hydroxyl ions would be expected to attack the 6-chloro group resulting in the formation of the impurity (III). However, contrary to the expectation of the skilled person, the process according to the invention results in bosentan having a purity of greater than 99%.

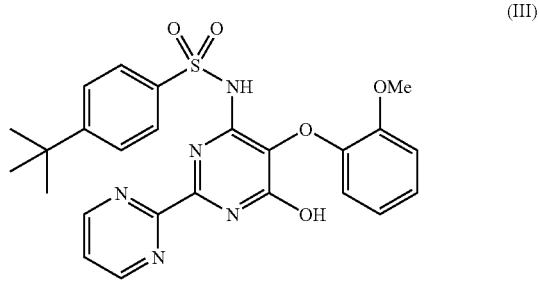 [SMILES: COc1ccccc1Oc1c(O)nc(-c2ncccn2)nc1NS(=O)(=O)c1ccc(C(C)(C)C)cc1]

(III)

In further embodiments of the invention, organic solvents that can be used include dimethyl sulfoxide, tetrahydrofuran, acetonitrile, dimethylformamide and dimethylacetamide. The preferred solvent is tetrahydrofuran, but of course it will be understood that the choice of solvent(s) will be governed by the ability to dissolve the ethylene glycol required by the invention. Accordingly, any solvent with the ability to dissolve ethylene glycol may be utilised in the working of this invention.

In processes according to the invention, 4-tert-butyl-N-[6-chloro-5-(2-methoxyphenoxy)-2-(2-pyrimidinyl)-pyrimidin-4-yl]-benzenesulfonamide is added to a mixture of ethylene glycol and hydroxide ions in a solvent. In preferred embodiments, the mixture is heated to substantially dissolve the 4-tert-butyl-N-[6-chloro-5-(2-methoxyphenoxy)-2-(2-pyrimidinyl)-pyrimidin-4-yl]-benzenesulfonamide. Preferably, the heating temperature is between about 40 and 95° C., most preferably about 50° C.

Further, preferred embodiments provide that the mixture comprising the 4-tert-butyl-N-[6-chloro-5-(2-methoxyphenoxy)-2-(2-pyrimidinyl)-pyrimidin-4-yl]-benzene-sulfonamide is stirred.

It has further been noted by the inventors that the prior art processes employ high temperatures in the preparation of bosentan. This further adds to the inefficiency and high processing costs. The high temperatures also increase the likelihood of impurities being formed during the process. Surprisingly, it has been found that the use of hydroxides ions in a process for preparing bosentan according to the invention facilitates the use of lower temperatures as compared to the prior art processes.

In certain embodiments, the reaction can be carried out at a temperature in the range of from 55-95° C. The preferred reaction temperature is from 65-75° C.

In certain embodiments an acid is added to the reaction mixture of ethylene glycol, hydroxide ions and bosentan. The acid serves to neutralise any excess hydroxide ions that may be present in the mixture. The acid may be an organic or inorganic acid. In certain embodiments, the acid may be an inorganic acid selected from the non-limiting group comprising: hydrochloric, hydrobromic, hydroiodic, nitric, sulfuric, and phosphoric acid. In preferred embodiments, the acid may be an organic acid selected from the group comprising: an aliphatic carboxylic acid, an aromatic carboxylic acid, and a sulfonic acid. Examples of organic acids that may be useful in the working of the present invention comprise formic, acetic, propionic, succinic, camphorsulfonic, citric, fumaric, gluconic, lactic, malic, mucic, tartaric, para-toluenesulfonic, glycolic, glucuronic, maleic, furoic, glutamic, benzoic, anthranilic, salicylic, phenylacetic, mandelic, pamoic, methanesulfonic, ethanesulfonic, pantothenic, benzenesulfonic (besylate), stearic, sulfanilic, alginic, galacturonic, 2-ethanedioic (oxalic), 3-propanedioic (malonic), 4-butanedioic (succinic), 5-pentanedioic (glutaric), 6-hexanedioic (adipic), cis-butenedioic (maleic) and trans-butenedioic (fumaric), dihydroxybutanedioic (tartaric), 2-hydroxypropane-1,2,3-tricarboxylic (citric), pimelic, suberic, azelaic, and sebacic acid. Monocarboxylic acids that may be useful in the working of the present invention include, but are not limited to, methanoic (formic), ethanoic (acetic), propanoic (propionic), butanoic (butyric), pentanoic (valeric), hexanoic (caproic), heptanoic (enanthic), 1-hydroxypropanoic (lactic), and 3-benzyl-2-propenoic (cinnamic) acid. In a particularly preferred embodiment the acid is tartaric acid.

This process according to the invention as herein described yields bosentan with a high yield of around 80-82% starting from the dichloro compound (I) and with >99% HPLC purity. Illustrative of the invention is a pharmaceutical composition made by mixing bosentan according to the invention and a pharmaceutically acceptable carrier. An example of the invention is a method for the treatment of an endothelin-receptor mediated disorder in a subject in need thereof, comprising administering to the subject a therapeutically effective amount of bosentan according to any of the embodiments of the invention or of a pharmaceutical composition described above. Also included in the invention is the use of bosentan substantially free of impurities, for the preparation of a medicament for treating an endothelin-receptor mediated disorder.

Pharmaceutical formulations of the present invention contain bosentan; it is preferred that the bosentan is substantially pure, but this is non-limiting to the working of the invention. The bosentan prepared by the processes of the present invention is ideal for pharmaceutical formulation. In addition to the active ingredient(s), the pharmaceutical compositions of the present invention may contain one or more excipients. Excipients are added to the composition for a variety of purposes. Diluents increase the bulk of a solid pharmaceutical composition and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. Carbopol®), carboxymethyl cellulose sodium, dextrin, ethyl cellulose, gelatin, guar gum, hydrogenated vegetable oil, hydroxyethyl cellulose, hydroxypropyl cellulose (e.g. Klucer), hydroxypropyl methyl cellulose (e.g. Methocel®), liquid glucose, magnesium aluminum silicate, maltodextrin, methyl cellulose, polymethacrylates, povidone (e.g. Kollidon®, Plasdone™), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethyl cellulose calcium, carboxymethyl cellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavouring agents and flavour enhancers make the dosage form more palatable to the patient. Common flavouring agents and flavour enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colourant to improve their appearance and/or facilitate patient identification of the product and unit dosage level.

In liquid pharmaceutical compositions of the present invention, bosentan and any other solid excipients are dissolved or suspended in a liquid carrier such as water, vegetable oil, alcohol, polyethylene glycol, propylene glycol or glycerin.

Liquid pharmaceutical compositions may further comprise emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel or organoleptic qualities of the product and/or coat the lining of the gastrointestinal tract. Such agents include acacia, alginic acid, bentonite, carbomer, carboxymethyl cellulose calcium or sodium, cetostearyl alcohol, methyl cellulose, ethyl cellulose, gelatin, guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxytoluene, butylated hydroxyanisole and ethylenediaminetetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate or sodium acetate.

Selection of excipients and the amounts used may be readily determined by the formulation scientist based upon experience and consideration of standard procedures and reference works in the field.

Solid compositions of the present invention include powders, granulates, aggregates and compacted compositions. Dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts. Dosage forms include solid dosage forms like tablets, powders, capsules, suppositories, sachets, troches and lozenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin or sorbitol, and an opacifying agent or colourant. The active ingredient and excipients may be formulated into compositions and dosage forms according to methods known in the art.

A composition for tableting or capsule filling may be prepared by wet granulation. In wet granulation, some or all of the active ingredient and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The following paragraphs enumerated consecutively from 1 through 44 provide for various aspects of the present invention. In one embodiment, the present invention provides:

1. A process for the preparation of bosentan (I), comprising the steps of:
(a) providing a mixture of ethylene glycol and hydroxide ions;
(b) adding 4-tert-butyl-N-[6-chloro-5-(2-methoxyphenoxy)-2-(2-pyrimidinyl)-pyrimidin-4-yl]-benzenesulfonamide to the mixture from step (a) or vice versa; and
(c) isolating bosentan (I) from the mixture obtained in step (b).
2. A process according to paragraph 1, wherein the ethylene glycol is dissolved in an organic solvent.
3. A process according to paragraph 2, wherein the organic solvent is dimethyl sulfoxide, tetrahydrofuran, acetonitrile, dimethylformamide or dimethylacetamide.
4. A process according to paragraph 3, wherein the organic solvent is tetrahydrofuran.
5. A process according to any one of paragraphs 2 to 4, wherein the ethylene glycol is dissolved by heating the organic solvent.
6. A process according to any one of the preceding paragraphs, wherein the mixture from step (b) is heated to dissolve the 4-tert-butyl-N-[6-chloro-5-(2-methoxyphenoxy)-2-(2-pyrimidinyl)-pyrimidin-4-yl]-benzenesulfonamide.
7. A process according to paragraph 5 or 6, wherein the mixtures from steps (a) and (b) are heated independently to a temperature in the range of between about 40 and 95° C.
8. A process according to paragraph 7, wherein the temperature is in the range of between 65 and 75° C.
9. A process according to any one of the preceding paragraphs, wherein the hydroxide ions are provided by an alkali metal hydroxide, an alkali earth metal hydroxide, or an ammonium hydroxide.
10. A process according to paragraph 9, wherein the hydroxide ions are provided by an alkali metal hydroxide.
11. A process according to paragraph 10, wherein the alkali metal hydroxide is sodium hydroxide, potassium hydroxide or lithium hydroxide.
12. A process according to paragraph 11, wherein the alkali metal hydroxide is sodium hydroxide.
13. A process according to any one of the preceding paragraphs, wherein the mixture from step (b) is cooled.
14. A process according to paragraph 13, wherein the mixture is cooled to a temperature of between 0 and 25° C.
15. A process according to any one of the preceding paragraphs, wherein an organic or inorganic acid is added to the mixture from step (b).
16. A process according to paragraph 15, wherein the inorganic acid is hydrochloric, hydrobromic, hydroiodic, nitric, sulfuric, or phosphoric acid.
17. A process according to paragraph 15, wherein the organic acid is an aliphatic carboxylic acid, an aromatic carboxylic acid, or a sulfonic acid.
18. A process according to paragraph 17, wherein the acid is formic, acetic, propionic, succinic, camphorsulfonic, citric, fumaric, gluconic, lactic, malic, mucic, tartaric, para-toluenesulfonic, glycolic, glucuronic, maleic, furoic, glutamic, benzoic, anthranilic, salicylic, phenylacetic, mandelic, pamoic, methanesulfonic, ethanesulfonic, pantothenic, benzenesulfonic (besylate), stearic, sulfanilic, alginic, galacturonic, 2-ethanedioic (oxalic), 3-propanedioic (malonic), 4-butanedioic (succinic), 5-pentanedioic (glutaric), 6-hexanedioic (adipic), cis-butenedioic (maleic), trans-butenedioic (fumaric), dihydroxybutanedioic (tartaric), 2-hydroxypropane-1,2,3-tricarboxylic (citric), pimelic, suberic, azelaic, or sebacic acid.
19. A process according to paragraph 17, wherein the acid is methanoic (formic), ethanoic (acetic), propanoic (propionic), butanoic (butyric), pentanoic (valeric), hexanoic (caproic), heptanoic (enanthic), 2-hydroxypropanoic (lactic), or 3-benzyl-2-propenoic (cinnamic) acid.
20. A process according to paragraph 18, wherein the acid is tartaric acid.
21. A process for the preparation of bosentan (I), comprising the steps of:
(a) heating a mixture of ethylene glycol and sodium hydroxide in tetrahydrofuran until the ethylene glycol has substantially dissolved;
(b) adding to the solution from step (a) 4-tert-butyl-N-[6-chloro-5-(2-methoxyphenoxy)-2-(2-pyrimidinyl)-pyrimidin-4-yl]-benzenesulfonamide or vice versa, and heating the mixture;
(c) cooling the mixture from step (b) and adding a solution of tartaric acid; and
(d) isolating the resulting solid.
22. A process according to paragraph 21, wherein the mixture in step (b) is heated to a temperature of between about 40 and 60° C.
23. A process according to paragraph 22, wherein the mixture is heated to about 50° C.
24. A process according to any one of paragraphs 21 to 23, wherein between steps (b) and (c) the tetrahydrofuran is removed from the reaction mixture by distillation under vacuum.
25. A process according to any one of paragraphs 21 to 24, wherein the mixture in step (c) is cooled to a temperature of between about 0-20° C.
26. A process according to paragraph 25, wherein the mixture is cooled to about 10° C.
27. A process according to any one of paragraphs 21 to 26, wherein the resultant solid is isolated by filtration.
28. A process according to paragraph 27, wherein the solid is further washed and dried.
29. A process according to paragraph 28, wherein the solid is washed with isopropyl alcohol, ethanol and water.
30. A process according to paragraph 28 or 29, wherein the solid is dried under vacuum.
31. Bosentan (I) comprising less than about 0.1% of the dimer impurity (II):

32. Bosentan (I) comprising less than about 5% of the 6-hydroxy-sulfonamide impurity (III):

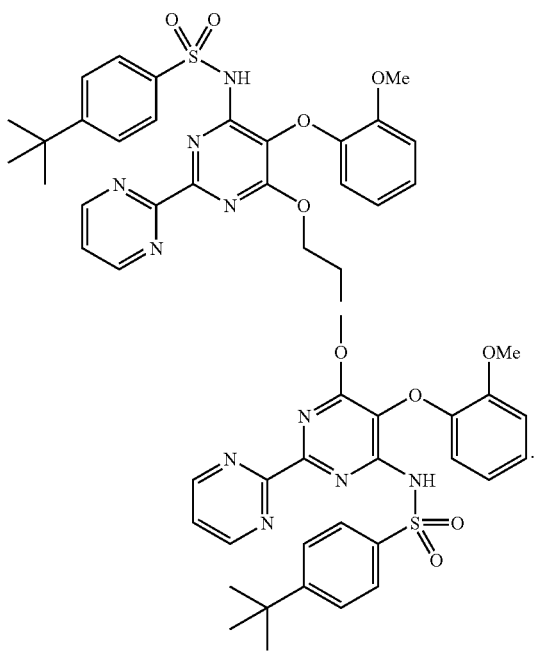

(II)

33. Bosentan (I) prepared by a process according to any one of paragraphs 1 to 30, comprising less than about 0.1% of the dimer impurity (II):

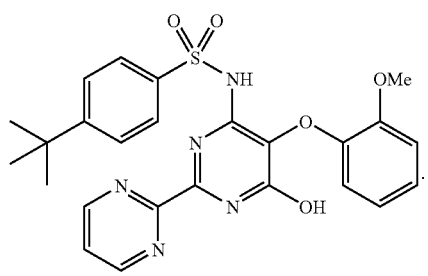

(II)

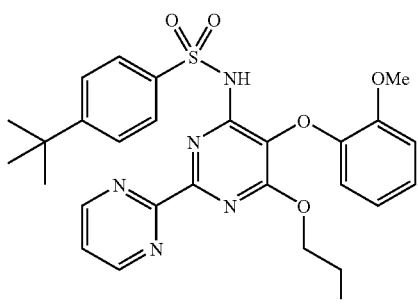

34. Bosentan (I) prepared by a process according to any one of paragraphs 1 to 30, comprising less than about 5% of the 6-hydroxy-sulfonamide impurity (III):

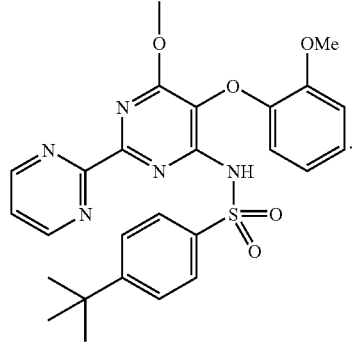

(III)

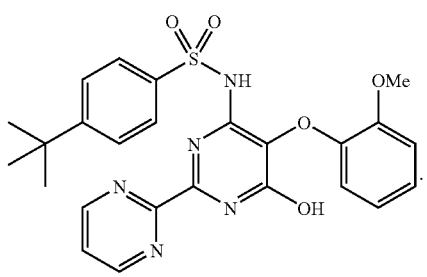

35. Bosentan (I) according to any one of paragraphs 31 to 34, for use in medicine.
36. Bosentan (I) according to paragraph 35, for treating an endothelin-receptor mediated disorder.
37. Bosentan (I) according to paragraph 36, wherein the disorder is pulmonary arterial hypertension.
38. Use of bosentan (I) according to any one of paragraphs 31 to 37, in the manufacture of a medicament for the treatment or prevention of an endothelin-receptor mediated disorder.
39. A use according to paragraph 38, wherein the disorder is pulmonary arterial hypertension.
40. A pharmaceutical composition comprising bosentan (I) according to any one of paragraphs 31 to 37, and at least one pharmaceutically acceptable excipient.
41. Use of a pharmaceutical composition according to paragraph 40, in the manufacture of a medicament for the treatment or prevention of an endothelin-receptor mediated disorder.
42. A use according to paragraph 41, wherein the disorder is pulmonary arterial hypertension.
43. A method of treating or preventing an endothelin-receptor mediated disorder, comprising administering a therapeutically or prophylactically effective amount of bosentan (I) according to any one of paragraphs 31 to 37, to a patient in need thereof.
44. A method according to paragraph 43, wherein the disorder is pulmonary arterial hypertension.

The details of the invention, its objects and advantages are explained hereunder in greater detail in relation to non-limiting exemplary illustrations.

EXAMPLE

Experimental Procedure for Preparing Bosentan (I)

Ethylene glycol (315.29 g, 107 eq) was mixed in tetrahydrofuran (175 ml, 7 vol) and sodium hydroxide (19.01 g, 10 eq) was added. The mixture was heated to 50° C. for 30 minutes or until the solution became clear. To the clear solution was added 4-tert-butyl-N-[6-chloro-5-(2-methoxyphenoxy)-2-(2-pyrimidinyl)-pyrimidin-4-yl]-benzenesulfonamide (25 g, 1 eq) at 50° C. and stirred at 65° C. for 12 hours. The tetrahydrofuran was distilled out under vacuum at 210-220 mbar pressure at 35° C. The resulting solution was cooled to 10° C., a solution of tartaric acid (35.65 g, 5 eq) in water (100 ml, 4 vol) was added and stirred for 1.5 hours at the same temperature. The resultant solid was filtered, washed with a mixture of isopropyl alcohol (100 ml, 4 vol), ethanol (50 ml, 2 vol) and water (200 ml, 8 vol), and dried under vacuum at 60° C. to obtain the product as an off-white solid.

Molar yield=85%
HPLC purity=99.07%
Impurity (II)=not detectable (as measured by HPLC)
Impurity (III)=0.3% (as measured by HPLC)

If desired, the bosentan (I) can be further purified, for example, by recrystallisation from one or more suitable solvents, such as ethanol and water.

What is claimed is:

1. A process for the preparation of bosentan (I), comprising the steps of:
   (a) providing a mixture of ethylene glycol and hydroxide ions;
   (b) adding 4-tert-butyl-N-[6-chloro-5-(2-methoxyphenoxy)-2-(2-pyrimidinyl)-pyrimidin-4-yl]-benzenesulfonamide to the mixture from step (a) or vice versa; and
   (c) isolating bosentan (I) from the mixture obtained in step (b).

2. A process according to claim 1, wherein:
   (i) the ethylene glycol is dissolved in an organic solvent; and/or
   (ii) the ethylene glycol is dissolved in dimethyl sulfoxide, tetrahydrofuran, acetonitrile, dimethylformamide or dimethylacetamide; and/or
   (iii) the ethylene glycol is dissolved in tetrahydrofuran; and/or
   (iv) the ethylene glycol is dissolved in an organic solvent by heating the organic solvent; and/or
   (v) the mixture from step (b) is heated to dissolve the 4-tert-butyl-N-[6-chloro-5-(2-methoxyphenoxy)-2-(2-pyrimidinyl)-pyrimidin-4-yl]-benzenesulfonamide; and/or
   (vi) the mixtures from steps (a) and (b) are heated independently to a temperature in the range of between about 40 and 95° C.; and/or
   (vii) the mixtures from steps (a) and (b) are heated independently to a temperature in the range of between about 65 and 75° C.; and/or
   (viii) the hydroxide ions are provided by an alkali metal hydroxide, an alkali earth metal hydroxide, or an ammonium hydroxide; and/or
   (ix) the hydroxide ions are provided by an alkali metal hydroxide; and/or
   (x) the hydroxide ions are provided by sodium hydroxide, potassium hydroxide or lithium hydroxide; and/or
   (xi) the hydroxide ions are provided by sodium hydroxide; and/or
   (xii) the mixture from step (b) is cooled; and/or
   (xiii) the mixture from step (b) is cooled to a temperature of between 0 and 25° C.; and/or
   (xiv) an organic or inorganic acid is added to the mixture from step (b); and/or
   (xv) an inorganic acid is added to the mixture from step (b), and wherein the inorganic acid is hydrochloric, hydrobromic, hydroiodic, nitric, sulfuric, or phosphoric acid; and/or
   (xvi) an organic acid is added to the mixture from step (b), and wherein the organic acid is an aliphatic carboxylic acid, an aromatic carboxylic acid, or a sulfonic acid; and/or
   (xvii) an organic acid is added to the mixture from step (b), and wherein the organic acid is formic, acetic, propionic, succinic, camphorsulfonic, citric, fumaric, gluconic, lactic, malic, mucic, tartaric, para-toluenesulfonic, glycolic, glucuronic, maleic, furoic, glutamic, benzoic, anthranilic, salicylic, phenylacetic, mandelic, pamoic, methanesulfonic, ethanesulfonic, pantothenic, benzenesulfonic (besylate), stearic, sulfanilic, alginic, galacturonic, 2-ethanedioic (oxalic), 3-propanedioic (malonic), 4-butanedioic (succinic), 5-pentanedioic (glutaric), 6-hexanedioic (adipic), cis-butenedioic (maleic), trans-butenedioic (fumaric), dihydroxybutanedioic (tartaric), 2-hydroxypropane-1,2,3-tricarboxylic (citric), pimelic, suberic, azelaic, or sebacic acid; and/or
   (xviii) an organic acid is added to the mixture from step (b), and wherein the organic acid is methanoic (formic), ethanoic (acetic), propanoic (propionic), butanoic (butyric), pentanoic (valeric), hexanoic (caproic), heptanoic (enanthic), 2-hydroxypropanoic (lactic), or 3-benzyl-2-propenoic (cinnamic) acid; and/or
   (xix) an organic acid is added to the mixture from step (b), and wherein the organic acid is tartaric acid.

3. Bosentan (I) prepared by a process according to claim 1, comprising less than about 0.1% of the dimer impurity (II):

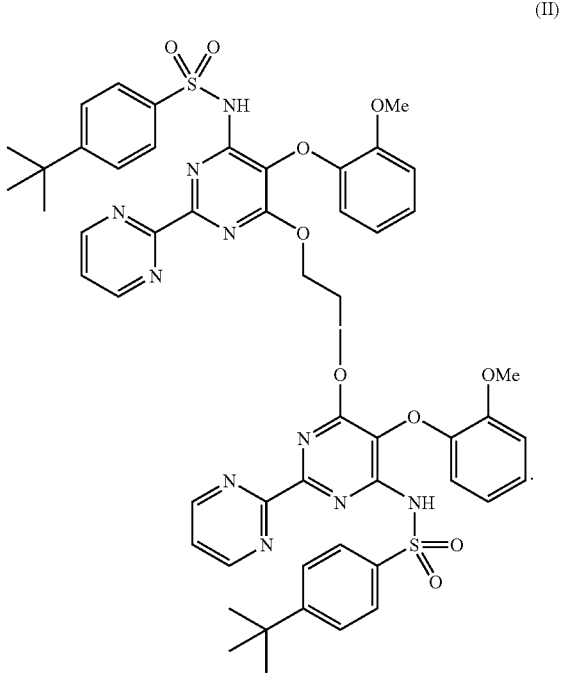 [SMILES: COc1ccccc1Oc1c(NS(=O)(=O)c2ccc(C(C)(C)C)cc2)nc(-c2ncccn2)nc1OCCOc1nc(-c2ncccn2)nc(NS(=O)(=O)c2ccc(C(C)(C)C)cc2)c1Oc1ccccc1OC]

4. Bosentan (I) prepared by a process according to claim 1, comprising less than about 5% of the 6-hydroxy-sulfonamide impurity (III):

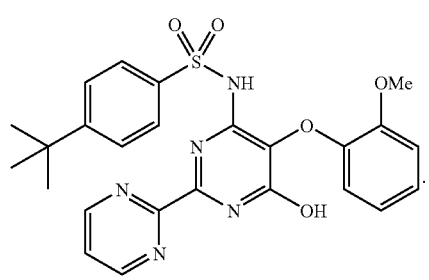
(III)
\* \* \* \* \*